United States Patent
Takagi

(10) Patent No.: US 8,481,310 B2
(45) Date of Patent: Jul. 9, 2013

(54) TAG PEPTIDE HAVING A PROTEASE RECOGNITION SEQUENCE AND USE THEREOF

(75) Inventor: Junichi Takagi, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/265,024

(22) PCT Filed: Apr. 21, 2010

(86) PCT No.: PCT/JP2010/057028
§ 371 (c)(1),
(2), (4) Date: Nov. 4, 2011

(87) PCT Pub. No.: WO2010/123013
PCT Pub. Date: Oct. 28, 2010

(65) Prior Publication Data
US 2012/0052569 A1    Mar. 1, 2012

(30) Foreign Application Priority Data
Apr. 22, 2009  (JP) .................................. 2009-103925

(51) Int. Cl.
*C12N 5/07*  (2010.01)
*C07K 4/00*  (2006.01)
*C12P 21/08* (2006.01)

(52) U.S. Cl.
USPC ......... 435/326; 530/300; 530/327; 530/387.9

(58) Field of Classification Search
None
See application file for complete search history.

(56) References Cited

U.S. PATENT DOCUMENTS

| | | | |
|---|---|---|---|
| 2002/0061513 A1 | 5/2002 | Seraphin et al. |
| 2005/0182243 A1 | 8/2005 | Sligar et al. |
| 2009/0042216 A1 | 2/2009 | Seraphin et al. |
| 2009/0306352 A1 | 12/2009 | Shaw et al. |
| 2011/0039331 A1 | 2/2011 | Takagi |

FOREIGN PATENT DOCUMENTS

| | | |
|---|---|---|
| EP | 0 960 939 | 12/1999 |
| JP | 2002-522085 | 7/2002 |
| JP | 2002-542261 | 12/2002 |
| JP | 2007-061057 | 3/2007 |
| JP | 2007-525490 | 9/2007 |
| JP | 2008-537884 | 10/2008 |
| WO | 00/63250 | 10/2000 |
| WO | 2009/096112 | 8/2009 |

OTHER PUBLICATIONS

Terpe et al. (Applied Microbiology Biotechnology. 2003; 60: 523-533).*
Kashmiri et al. (Methods. 2005; 36:25-34).*
Tamura et al. (Journal of Immunology. 2000; 164 (3):1432-1441).*
Greenspan et al (Nature Biotechnology. 7; 10:936-937 (1999).*
van den Berg et al. (Proteomics. 2012; 12: 516-529).*
English translation of International Preliminary Report on Patentability and Written Opinion dated Nov. 22, 2011.
D. S. Waugh, Making the Most of Affinity Tags, TRENDS in Biotechnology, vol. 23, No. 6, pp. 316-320, Jun. 2005.
O. Puig et al., "The Tandem Affmity Purification (TAP) Method: A General Procedure of Protein Complex Purification", METHODS, vol. 24, pp. 218-229, 2001.
T. Nogi et al., "Novel Affinity Tag System Using Structurally Defined Antibody-Tag Interaction: Application to Single-Step Protein Purification", Protein Science, vol. 17, pp. 2120-2126, 2008.
S. Tabata et al., "Analysis of Rat Monoclonal Antibody 2H5 that Binds 11-Residues TEV Protease Recognition Sequence", The $9^{th}$ Annual Meeting of the Protein Science Society of Japan, a poster session, May 21, 2009.
Extended European Search Report issued Apr. 17, 2013 in corresponding European Patent Application No. 10767070.5.
A. Einhauer et al., "The FLAG™ peptide, a versatile fusion tag for the purification of recombinant proteins", Journal of Biochemical and Biophysical Methods, vol. 49, Nos. 1-3, 2001, pp. 455-465.
T. Hosfield et al., "Versatile Epitope Tagging Vector for Gene Expression in Mammalian Cells", Biotechniques, vol. 25, No. 2, 1998, pp. 306-309.

* cited by examiner

*Primary Examiner* — Shanon A Foley
(74) *Attorney, Agent, or Firm* — Wenderoth, Lind & Ponack, L.L.P.

(57) ABSTRACT

Provided is a tag peptide in which a protease recognition sequence and an epitope of an antibody against the tag peptide are overlapped and thereby the protease recognition sequence per se is usable for detection or purification. Also provided is a purification method for recombinant proteins using the tag peptide and an antibody thereagainst. A preferable tag peptide comprises a Tobacco etch virus (TEV) protease recognition sequence as the protease recognition sequence, and its examples include a tag peptide comprising the amino acid sequence (1): $RX_1X_2LYX_3QGKDG$ (wherein $X_1$, $X_2$ and $X_3$ may be the same or different and represent any amino acid residue).

4 Claims, 10 Drawing Sheets

(a)

(b)

(a)

(b)

double tag

Fig. 3

| | | |
|---|---|---|
| TEV-Fn | Met - RENLYPQGKDGS - Fn | SEQ ID NO: 11 |
| His-eTEV-Fn | Met -G- Hisx10 - SSGHIEGRHMRENLYFQGKDGS - Fn | SEQ ID NO: 12 |
| His-eTEV(M0A)-Fn | Met -G- Hisx10 - SSGHIEGRHARENLYFQGKDGS - Fn | SEQ ID NO: 13 |
| His-eTEV(R1A)-Fn | Met -G- Hisx10 - SSGHIEGRHMAENLYFQGKDGS - Fn | SEQ ID NO: 14 |
| His-eTEV(E2A)-Fn | Met -G- Hisx10 - SSGHIEGRHMRANLYFQGKDGS - Fn | SEQ ID NO: 15 |
| His-eTEV(N3A)-Fn | Met -G- Hisx10 - SSGHIEGRHMREALYFQGKDGS - Fn | SEQ ID NO: 16 |
| His-eTEV(L4A)-Fn | Met -G- Hisx10 - SSGHIEGRHMRENAYFQGKDGS - Fn | SEQ ID NO: 17 |
| His-eTEV(Y5A)-Fn | Met -G- Hisx10 - SSGHIEGRHMRENLAFQGKDGS - Fn | SEQ ID NO: 18 |
| His-eTEV(F6A)-Fn | Met -G- Hisx10 - SSGHIEGRHMRENLYAQGKDGS - Fn | SEQ ID NO: 19 |
| His-eTEV(Q7A)-Fn | Met -G- Hisx10 - SSGHIEGRHMRENLYFAGKDGS - Fn | SEQ ID NO: 20 |
| His-eTEV(G8A)-Fn | Met -G- Hisx10 - SSGHIEGRHMRENLYFQAKDGS - Fn | SEQ ID NO: 21 |
| His-eTEV(K9A)-Fn | Met -G- Hisx10 - SSGHIEGRHMRENLYFQGADGS - Fn | SEQ ID NO: 22 |
| His-eTEV(D10A)-Fn | Met -G- Hisx10 - SSGHIEGRHMRENLYFQGKAGS - Fn | SEQ ID NO: 23 |
| His-eTEV(G11A)-Fn | Met -G- Hisx10 - SSGHIEGRHMRENLYFQGKDAS - Fn | SEQ ID NO: 24 |

Fig. 4

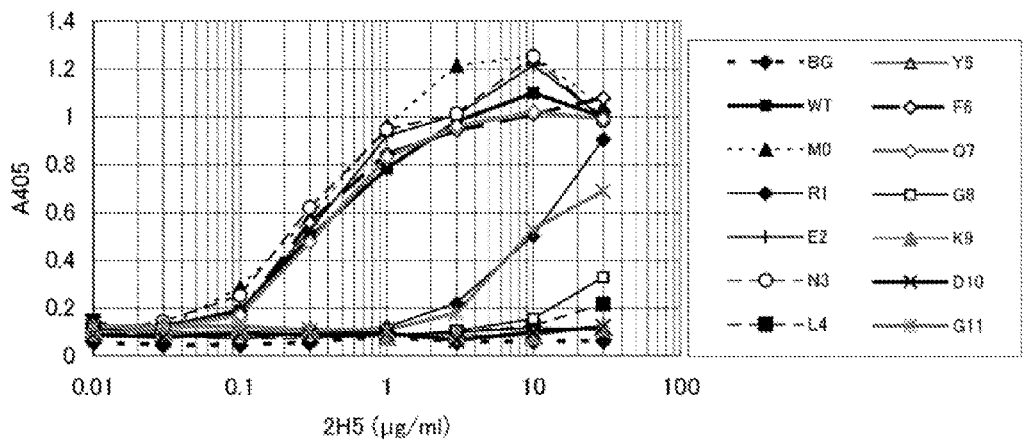

Fig. 5

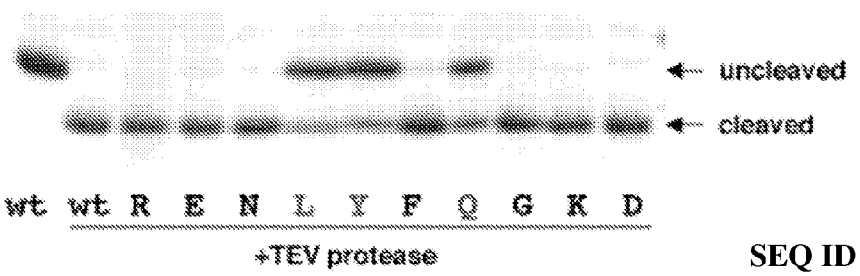

wt  wt  R  E  N  L  Y  F  Q  G  K  D
        +TEV protease

SEQ ID NO: 25

Fig. 8
eTEV-NP1
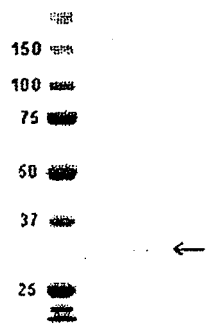
[Fig. 9]
eTEV-EGFP
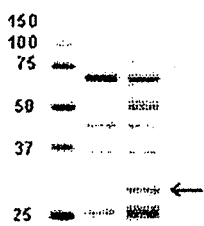

hGH-eTEV-sema6C sema3A-eTEV

Fig. 12

```
1                                                              60
MCYPCQVEYPEQVCYPCQVSRENLYFQGKDGSPVEKMSKGEELFTGVVPILVELDGDVNG
      P4C3 tag         eTEV tag         GFPuv
61                                                             120
HKFSVSGEGEGDATYGKLTLKFICTTGKLPVPWPTLVTTFSYGVQCFSRYPDHMKRHDFF
121                                                            180
KSAMPEGYVQERTISFKDDGNYKTRAEVKFEGDTLVNRIELKGIDFKEDGNILGHKLEYN
181                                                            240
YNSHNVYITADKQKNGIKANFKIRHNIEDGSVQLADHYQQNTPIGDGPVLLPDNHYLSTQ
241
SALSKDPNEKRDHMVLLEFVTAAGITHGMDELYKTGHHHHHH
           GFPuv            Hisx6
```

SEQ ID NO: 9

Fig. 13

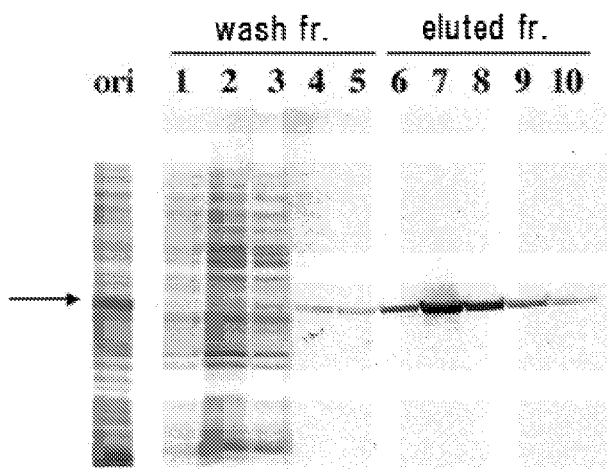

Fig. 14
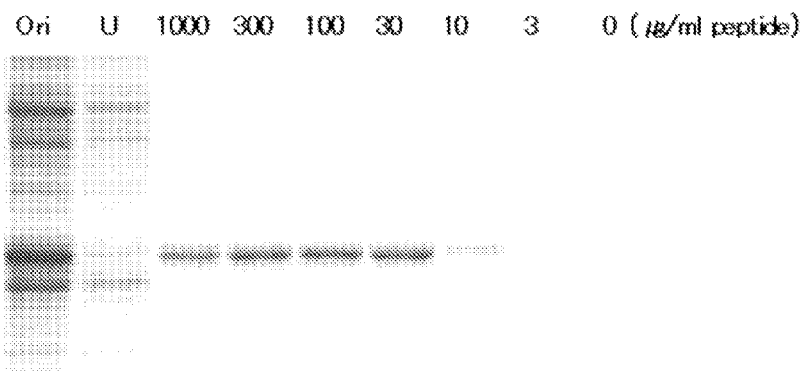
Fig. 15
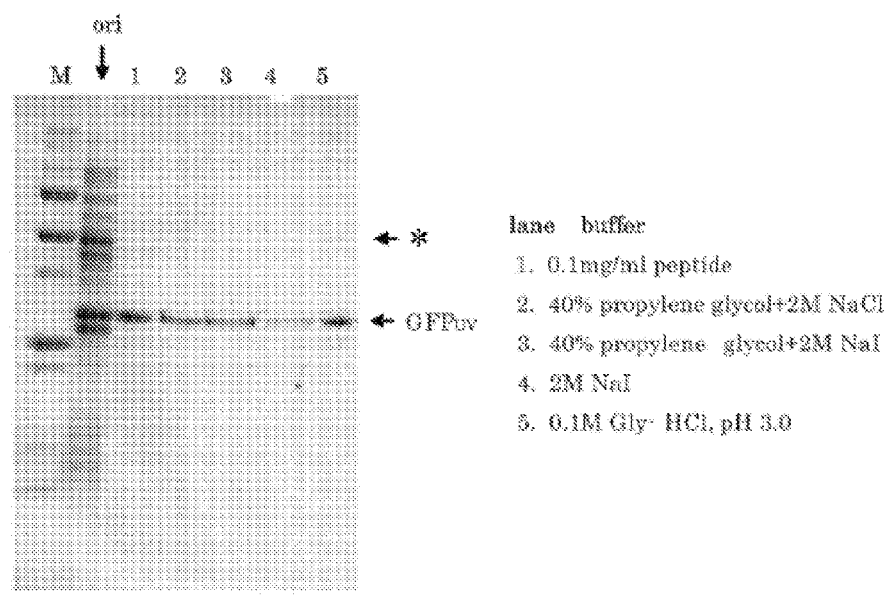
| lane | buffer |
|------|--------|
| 1. | 0.1 mg/ml peptide |
| 2. | 40% propylene glycol+2M NaCl |
| 3. | 40% propylene glycol+2M NaI |
| 4. | 2M NaI |
| 5. | 0.1M Gly·HCl, pH 3.0 |
Fig. 16
```
1                                 33
GYPGQYPGQYPGQYPGQYPGQVRENLYFQGKDG
    Target(X5) tag       eTEV tag
```
SEQ ID NO: 10

SEQUENCE LISTING

```
<160> NUMBER OF SEQ ID NOS: 25

<210> SEQ ID NO 1
<211> LENGTH: 11
<212> TYPE: PRT
<213> ORGANISM: Artificial Sequence
<220> FEATURE:
<223> OTHER INFORMATION: Synthetic construct: tag peptide
<220> FEATURE:
<221> NAME/KEY: MISC_FEATURE
<222> LOCATION: (2)..(2)
<223> OTHER INFORMATION: Xaa stands for any amino-acid.
<220> FEATURE:
<221> NAME/KEY: MISC_FEATURE
<222> LOCATION: (3)..(3)
<223> OTHER INFORMATION: Xaa stands for any amino-acid.
<220> FEATURE:
<221> NAME/KEY: MISC_FEATURE
<222> LOCATION: (6)..(6)
<223> OTHER INFORMATION: Xaa stands for any amino-acid.

<400> SEQUENCE: 1

Arg Xaa Xaa Leu Tyr Xaa Gln Gly Lys Asp Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic construct: tag peptide

<400> SEQUENCE: 2

Arg Glu Asn Leu Tyr Phe Gln Gly Lys Asp Gly
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic construct: TEV protease recognition
      sequence

<400> SEQUENCE: 3

Glu Asn Leu Tyr Phe Gln Gly
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic construct: tag peptide
```

-continued

<400> SEQUENCE: 4

Met Arg Glu Asn Leu Tyr Phe Gln Gly Lys Asp Gly
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Synthetic construct: tag peptide

<400> SEQUENCE: 5

Tyr Pro Gly Gln
1

<210> SEQ ID NO 6
<211> LENGTH: 33
<212> TYPE: DNA
<213> ORGANISM: Artificial Sequence
<220> FEATURE:
<223> OTHER INFORMATION: Synthetic construct: eTEV peptide

<400> SEQUENCE: 6
cgcgagaacc tgtacttcca gggaaaggac gga                          33

<210> SEQ ID NO 7
<211> LENGTH: 99
<212> TYPE: DNA
<213> ORGANISM: Artificial Sequence
<220> FEATURE:
<223> OTHER INFORMATION: Synthetic construct: double tag

<400> SEQUENCE: 7 gggtacccccg acaatatcc aggtcagtat cctgggcaat atcccggtca gtacccaggc   60
caagtccgcg agaacctgta cttccaggga aaggacgga                         99

<210> SEQ ID NO 8
<211> LENGTH: 11
<212> TYPE: PRT
<213> ORGANISM: Artificial Sequence
<220> FEATURE:
<223> OTHER INFORMATION: Synthetic construct: antigen peptide

<400> SEQUENCE: 8

Arg Glu Asn Leu Tyr Phe Gln Gly Lys Asp Cys
1               5                   10

<210> SEQ ID NO 9
<211> LENGTH: 282
<212> TYPE: PRT
<213> ORGANISM: Artificial Sequence
<220> FEATURE:
<223> OTHER INFORMATION: Synthetic construct: GFPuv having eTEV tag

<400> SEQUENCE: 9

Met Gly Tyr Pro Gly Gln Val Gly Tyr Pro Gly Gln Val Gly Tyr Pro
1               5                   10                  15

Gly Gln Val Ser Arg Glu Asn Leu Tyr Phe Gln Gly Lys Asp Gly Ser
            20                  25                  30

Pro Val Glu Lys Met Ser Lys Gly Glu Glu Leu Phe Thr Gly Val Val
        35                  40                  45

Pro Ile Leu Val Glu Leu Asp Gly Asp Val Asn Gly His Lys Phe Ser
    50                  55                  60

```
Val Ser Gly Glu Gly Glu Gly Asp Ala Thr Tyr Gly Lys Leu Thr Leu
 65                  70                  75                  80

Lys Phe Ile Cys Thr Thr Gly Lys Leu Pro Val Pro Trp Pro Thr Leu
                 85                  90                  95

Val Thr Thr Phe Ser Tyr Gly Val Gln Cys Phe Ser Arg Tyr Pro Asp
            100                 105                 110

His Met Lys Arg His Asp Phe Phe Lys Ser Ala Met Pro Glu Gly Tyr
        115                 120                 125

Val Gln Glu Arg Thr Ile Ser Phe Lys Asp Asp Gly Asn Tyr Lys Thr
130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Asn Ser His Asn Val Tyr Ile Thr Ala Asp Lys
            180                 185                 190

Gln Lys Asn Gly Ile Lys Ala Asn Phe Lys Ile Arg His Asn Ile Glu
        195                 200                 205

Asp Gly Ser Val Gln Leu Ala Asp His Tyr Gln Gln Asn Thr Pro Ile
    210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr His Gly Met Asp Glu Leu
            260                 265                 270

Tyr Lys Thr Gly His His His His His
        275                 280

<210> SEQ ID NO 10
<211> LENGTH: 33
<212> TYPE: PRT
<213> ORGANISM: Artificial Sequence
<220> FEATURE:
<223> OTHER INFORMATION: Synthetic construct: double tag

<400> SEQUENCE: 10

Gly Tyr Pro Gly Gln Tyr Pro Gly Gln Tyr Pro Gly Gln Tyr Pro Gly
1               5                  10                  15

Gln Tyr Pro Gly Gln Val Arg Glu Asn Leu Tyr Phe Gln Gly Lys Asp
            20                  25                  30

Gly

<210> SEQ ID NO 11
<211> LENGTH: 13
<212> TYPE: PRT
<213> ORGANISM: Artificial Sequence
<220> FEATURE:
<223> OTHER INFORMATION: Synthetic construct: tag peptide fusion protein

<400> SEQUENCE: 11

Met Arg Glu Asn Leu Tyr Phe Gln Gly Lys Asp Gly Ser
1               5                  10

<210> SEQ ID NO 12
<211> LENGTH: 34
<212> TYPE: PRT
<213> ORGANISM: Artificial Sequence
<220> FEATURE:
<223> OTHER INFORMATION: Synthetic construct: tag peptide fusion protein
```

-continued

```
<400> SEQUENCE: 12

Met Gly His His His His His His His His His Ser Ser Gly His
1               5                   10                  15

Ile Glu Gly Arg His Met Arg Glu Asn Leu Tyr Phe Gln Gly Lys Asp
            20                  25                  30

Gly Ser

<210> SEQ ID NO 13
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 13

Met Gly His His His His His His His His His Ser Ser Gly His
1               5                   10                  15

Ile Glu Gly Arg His Ala Arg Glu Asn Leu Tyr Phe Gln Gly Lys Asp
            20                  25                  30

Gly Ser

<210> SEQ ID NO 14
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 14

Met Gly His His His His His His His His His Ser Ser Gly His
1               5                   10                  15

Ile Glu Gly Arg His Met Ala Glu Asn Leu Tyr Phe Gln Gly Lys Asp
            20                  25                  30

Gly Ser

<210> SEQ ID NO 15
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 15

Met Gly His His His His His His His His His Ser Ser Gly His
1               5                   10                  15

Ile Glu Gly Arg His Met Arg Ala Asn Leu Tyr Phe Gln Gly Lys Asp
            20                  25                  30

Gly Ser

<210> SEQ ID NO 16
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 16

Met Gly His His His His His His His His His Ser Ser Gly His
1               5                   10                  15

Ile Glu Gly Arg His Met Arg Glu Ala Leu Tyr Phe Gln Gly Lys Asp
            20                  25                  30
```

<210> SEQ ID NO 17
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 17

```
Met Gly His His His His His His His His His Ser Ser Gly His
1               5                   10                  15

Ile Glu Gly Arg His Met Arg Glu Asn Ala Tyr Phe Gln Gly Lys Asp
            20                  25                  30

Gly Ser
```

<210> SEQ ID NO 18
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 18

```
Met Gly His His His His His His His His His Ser Ser Gly His
1               5                   10                  15

Ile Glu Gly Arg His Met Arg Glu Asn Leu Ala Phe Gln Gly Lys Asp
            20                  25                  30

Gly Ser
```

<210> SEQ ID NO 19
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 19

```
Met Gly His His His His His His His His His Ser Ser Gly His
1               5                   10                  15

Ile Glu Gly Arg His Met Arg Glu Asn Leu Tyr Ala Gln Gly Lys Asp
            20                  25                  30

Gly Ser
```

<210> SEQ ID NO 20
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 20

```
Met Gly His His His His His His His His His Ser Ser Gly His
1               5                   10                  15

Ile Glu Gly Arg His Met Arg Glu Asn Leu Tyr Phe Ala Gly Lys Asp
            20                  25                  30

Gly Ser
```

<210> SEQ ID NO 21
<211> LENGTH: 34
<212> TYPE: PRT
<213> ORGANISM: Artificial Sequence

```
<220> FEATURE:
<223> OTHER INFORMATION: Synthetic construct: tag peptide fusion protein

<400> SEQUENCE: 21

Met Gly His His His His His His His His His Ser Ser Gly His
1               5                   10                  15

Ile Glu Gly Arg His Met Arg Glu Asn Leu Tyr Phe Gln Ala Lys Asp
            20                  25                  30

Gly Ser

<210> SEQ ID NO 22
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 22

Met Gly His His His His His His His His His Ser Ser Gly His
1               5                   10                  15

Ile Glu Gly Arg His Met Arg Glu Asn Leu Tyr Phe Gln Gly Ala Asp
            20                  25                  30

Gly Ser

<210> SEQ ID NO 23
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 23

Met Gly His His His His His His His His His Ser Ser Gly His
1               5                   10                  15

Ile Glu Gly Arg His Met Arg Glu Asn Leu Tyr Phe Gln Gly Lys Ala
            20                  25                  30

Gly Ser

<210> SEQ ID NO 24
<211> LENGTH: 34
<212> TYPE: PRT
<213> ORGANISM: Artificial Sequence
<220> FEATURE:
<223> OTHER INFORMATION: Synthetic construct: tag peptide fusion protein

<400> SEQUENCE: 24

Met Gly His His His His His His His His His Ser Ser Gly His
1               5                   10                  15

Ile Glu Gly Arg His Met Arg Glu Asn Leu Tyr Phe Gln Gly Lys Asp
            20                  25                  30

Ala Ser

<210> SEQ ID NO 25
<211> LENGTH: 10
<212> TYPE: PRT
<213> ORGANISM: Artificial Sequence
<220> FEATURE:
<223> OTHER INFORMATION: Synthetic construct: tag peptide

<400> SEQUENCE: 25

Arg Glu Asn Leu Tyr Phe Gln Gly Lys Asp
1               5                   10
```

TAG PEPTIDE HAVING A PROTEASE RECOGNITION SEQUENCE AND USE THEREOF

This application is a U.S. national stage of International Application No. PCT/JP2010/057028 filed Apr. 21, 2010.

TECHNICAL FIELD

The present invention relates to a tag peptide having a protease recognition sequence and use thereof. In particular, the present invention relates to a tag peptide having a protease recognition sequence, a polynucleotide encoding the tag peptide, a recombinant vector containing the polynucleotide, an antibody against the tag peptide and a purification method for proteins using the antibody.

BACKGROUND ART

In the life science field, preparation of recombinant proteins is widely performed as a part of basic research, applied research and product development. For detection and purification of recombinant proteins expressed in *Escherichia coli* or animal cells, adding a tag, i.e., a peptide of several residues, to the terminus of an objective protein is usually performed. However, since the tag is considered to affect the bioactivity, the crystal structure and the like of the objective protein, the tag must be ultimately separated off. Therefore, it is necessary to insert a specific protease recognition sequence between the tag and the objective protein.

For example, Non Patent Literature 1 describes a complex tag composed of a histidine tag in combination with an MBP (maltose binding protein) tag and a Tobacco etch virus (hereinafter referred to as "TEV") protease recognition sequence. Non Patent Literature 2 also describes a complex tag composed of protein A in combination with calmodulin binding peptide (CBP) and a TEV protease recognition sequence. However, in each of the above literature, the TEV protease recognition sequence is used only for separation of the added tag, and is not used per se as a tag for detection and purification. Use of a protease recognition sequence per se as a tag for detection and purification is expected to greatly simplify the design of the construct.

CITATION LIST

Non Patent Literature

Non Patent Literature 1:
David S. Waugh, Making the most of affinity tags. TRENDS in Biotechnology, Vol. 23, No. 6, June, 316-320 (2005)
Non Patent Literature 2:
Oscar Puig, et al., The Tandem Affinity Purification (TAP) Method: A General Procedure of Protein Complex Purification. METHODS 24, 218-229 (2001)

SUMMARY OF INVENTION

Technical Problem

An object of the present invention is to provide a tag peptide having a protease recognition sequence per se usable for detection and purification, and is also to provide a purification method for recombinant proteins using the tag peptide and an antibody thereagainst. Another object of the present invention is to provide a tag peptide comprising the tag peptide in combination with a second tag peptide and allowing two different antibodies to simultaneously bind thereto.

Solution to Problem

The present invention includes the following as a solution to the above-mentioned problems.
[1] A tag peptide having a protease recognition sequence, the protease recognition sequence overlapping with an epitope of an antibody against the tag peptide.
[2] A tag peptide having a protease recognition sequence, the protease recognition sequence overlapping with an epitope of an antibody against the tag peptide and being a Tobacco etch virus (TEV) protease recognition sequence.
[3] The tag peptide according to the above [1] or [2], comprising the following amino acid sequence (1):

(1)    $RX_1X_2LYX_3QGKDG$    (SEQ ID NO: 1)

(wherein $X_1$, $X_2$ and $X_3$ may be the same or different and represent any amino acid residue).
[4] The tag peptide according to the above [3], wherein the amino acid sequence (1) is the following amino acid sequence (2):

(2)    RENLYFQGKDG.    (SEQ ID NO: 2)

[5] A tag peptide comprising the tag peptide according to any of the above [1] to [4] in combination with a second tag peptide.
[6] The tag peptide according to the above [5], wherein the tag peptide allows an antibody against the tag peptide according to any of the above [1] to [4] and an antibody against the second tag peptide to simultaneously bind thereto.
[7] A polynucleotide encoding the tag peptide according to any of the above [1] to [6].
[8] A recombinant vector containing the polynucleotide according to the above [7].
[9] An antibody against the tag peptide according to any of the above [1] to [4].
[10] The antibody according to the above [9] which is a monoclonal antibody produced by rat-mouse hybridoma 2H5 (FERM BP-11245).
[11] Rat-mouse hybridoma 2H5 (FERN BP-11245).
[12] A purification method for proteins, comprising the following steps (i) to (iii):
(i) making the antibody according to the above [9] or [10] act on a sample containing a fusion protein of an objective protein and the tag peptide according to any of the above [1] to [4] for formation of a complex of the antibody with the fusion protein;
(ii) making an eluent act on the complex obtained in the step (i) for release of the fusion protein from the antibody; and
(iii) separating off the tag peptide by cleavage of the fusion protein obtained in the step (ii).
[13] A kit for protein expression, purification, detection or quantification, comprising the recombinant vector according to the above [8] or the antibody according to the above [9] or [10].

Advantageous Effect of Invention

According to the present invention, a tag peptide having a protease recognition sequence and an antibody against the tag peptide can be provided. By use of the tag peptide and the antibody thereagainst, an objective protein fused with the tag peptide can be highly purified in an easy manner and the tag peptide can be easily separated off.

According to the present invention, a tag peptide comprising the tag peptide having a protease recognition sequence in combination with a second tag peptide is provided. To the tag peptide, two different antibodies can simultaneously bind. Thus, even in the case where the antibody against an objective protein is not easily available, sandwich ELISA etc. can be utilized for detection of the objective protein in a minute amount. Therefore, according to the present invention, even an unskilled person can easily purify or detect a minute amount of unstable recombinant proteins that are expressed from cloned genes. Furthermore, the amounts of an objective protein in plural samples can be compared with one another in a high accuracy.

BRIEF DESCRIPTION OF DRAWINGS

FIG. 3 is a schematic view showing tag peptide fusion proteins each having a different TEV sequence linked to the N-terminus of the 9th to 10th region of the Fn3 domain of human fibronectin.

FIG. 4 shows the analysis results of the epitope of the monoclonal antibody 2H5.

FIG. 5 shows the analysis results of the amino acid(s) essential for recognition and cleavage by TEV protease.

FIG. 8 shows the results of eTEV-NP1 purification using 2H5 antibody-immobilized sepharose from the culture supernatant of eTEV-NP1-expressing HEK293T cells.

FIG. 9 shows the results of eTEV-EGFP purification using 2H5 antibody-immobilized sepharose from the culture supernatant of eTEV-EGFP-expressing HEK293T cells.

FIG. 12 shows the amino acid sequence of the $GFP_{UV}$-tag peptide fusion protein.

FIG. 13 shows the SDS gel electrophoresis results of eTEV-$GFP_{UV}$ purified by use of 2H5 antibody-immobilized sepharose.

FIG. 14 shows the examination results on the elution conditions (competitive peptide concentration) for eTEV-$GFP_{UV}$ bound to 2H5 antibody-immobilized sepharose.

FIG. 15 shows the examination results on the elution conditions (the kind of buffer solution) for eTEV-$GFP_{UV}$ bound to 2H5 antibody-immobilized sepharose.

FIG. 16 shows the amino acid sequence of the double tag in which the target tag and the eTEV tag are linked to each other.

DESCRIPTION OF EMBODIMENTS

[Tag Peptide]

The tag peptide of the present invention comprises an epitope of an antibody against the tag peptide, and a protease recognition sequence, and the epitope and the protease recognition sequence are overlapped. A condition that the epitope and the protease recognition sequence are overlapped means a condition that recognition (cleavage) by protease is not possible without the epitope region in the tag peptide, or a condition that recognition (specific binding) by an antibody against the tag peptide is not possible without the protease recognition sequence in the tag peptide. More preferred is a condition that recognition (cleavage) by protease is not possible without the epitope region in the tag peptide, and that recognition (specific binding) by an antibody against the tag peptide is not possible without the protease recognition sequence in the tag peptide.

Therefore, protease cleavage of an objective protein linked to the tag peptide of the present invention prevents recognition by the antibody against the tag peptide, and thus the objective protein can be changed into a form incapable of binding to an antibody-immobilized support etc. In addition, whether or not the tag peptide is successfully separated off by protease treatment can be checked by testing the binding of the objective protein to the antibody. This is particularly advantageous in the case where the molecular weight change by separation of the tag peptide is unclear.

In the tag peptide of the present invention, as long as the epitope of an antibody against the tag peptide and the protease recognition sequence are in the above-mentioned condition, it is enough for the overlap between them to contain at least one amino acid. It is particularly preferred that the epitope region contains the protease recognition sequence, that the protease recognition sequence contains the epitope region, or that the epitope region matches the protease recognition sequence.

Figure 1A:
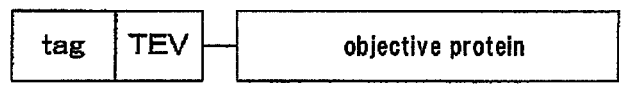
FIG. 1(a) is a schematic view showing a fusion protein of a tag peptide, a protease recognition sequence and an objective protein.
Figure 1B:
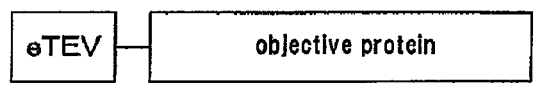
FIG. 1(b) is a schematic view showing a fusion protein of an objective protein and the tag peptide having a protease recognition sequence of the present invention.

Regarding an objective protein fused with a tag peptide, it cannot be denied that the tag peptide affects somewhat the bioactivity, the crystal structure and the like of the objective protein. Thus, after purification of the objective protein using the tag peptide, the tag peptide must be separated off. Conventionally, as shown in FIG. 1(a), it is necessary to insert a protease recognition sequence ("TEV" in FIG. 1(a)) in addition to a tag peptide ("tag" in FIG. 1(a)). In contrast, since the tag peptide of the present invention ("eTEV" in FIG. 1(b)) has a protease recognition sequence, it is not necessary to additionally insert a protease recognition sequence, as shown in FIG. 1(b). As a result, the design of a construct can be greatly simplified, and accordingly, the production time and cost of the construct can be significantly decreased. Further, although too long a tag sequence region may give an unexpected adverse effect on protein functions, such a risk can also be reduced.

The protease used for separation of the tag peptide is not particularly limited unless the protease nonspecifically cleaves an objective protein fused with the tag peptide. That is, the tag peptide of the present invention is a tag peptide having a protease recognition sequence, and the protease that recognizes the protease recognition sequence and catalyzes cleavage is preferably characterized by not nonspecifically cleaving an objective protein fused with the tag peptide. Specific examples of the protease include TEV protease, human rhinovirus (HRV) protease, enterokinase (EK), thrombin (Tb) and factor Xa (Xa). The protease recognition sequence is determined depending on the protease to be used. Regarding a protease generally characterized by nonspecific cleavage (for example, a protease which recognizes only one amino acid, such as trypsin), as long as its recognition sequence is contained not in the objective protein but only in the tag peptide, the recognition sequence for such a protease can be used as the protease recognition sequence of the tag peptide of the present invention.

The tag peptide of the present invention preferably comprises the following amino acid sequence (1).
Amino acid sequence (1): $RX_1X_2LYX_3QGKDG$ (SEQ ID NO: 1)
(wherein $X_1$, $X_2$ and $X_3$ may be the same or different and represent any amino acid residue.)

The amino acid sequence (1) has R at residue 1, L at residue 4, Y at residue 5, G at residue 8, K at residue 9, D at residue 10 and G at residue 11, each essential for the epitope of the 2H5 antibody mentioned later, and has a sequence based on the TEV protease recognition sequence ENLYFQG (SEQ ID NO: 3) in which the L, Y and Q vital for the substrate of the protease are conserved. In the amino acid sequence (1), $X_1$ is not particularly limited, but glutamic acid (E) is preferable, for example. $X_2$ is not particularly limited, but asparagine (N) is preferable, for example. $X_3$ is not particularly limited, but phenylalanine (F) is preferable, for example.

The tag peptide of the present invention particularly preferably comprises the following amino acid sequence (2).
Amino acid sequence (2): RENLYFQGKDG (SEQ ID NO: 2)

The amino acid sequence (2) is a sequence of the amino acid sequence (1) in which glutamic acid (E), asparagine (N) and phenylalanine (F) are selected as $X_1$, $X_2$ and $X_3$, respectively. Hereinafter, the amino acid sequence (2) is referred to as "eTEV sequence", a peptide comprising the eTEV sequence is referred to as "eTEV peptide", and a tag peptide comprising the eTEV peptide is referred to as "eTEV tag". The "eTEV peptide" and the "eTEV tag" also include a 12-amino-acid peptide (MRENLYFQGKDG (SEQ ID NO: 4)) having additional N-terminal methionine derived from the initiation codon.

As another embodiment of the tag peptide of the present invention, a tag peptide comprising the above-mentioned tag peptide having a protease recognition sequence in combination with a second tag peptide is provided. The second tag peptide is not particularly limited and can be appropriately selected from known tag peptides. Preferred is a tag peptide recognizable by a specific antibody. Specific examples thereof include FLAG tag, MYC tag, HA tag and V5 tag. Preferably used as the second tag peptide is, for example, a tag peptide comprising an amino acid sequence having the motif YPGQ (SEQ ID NO: 5) repeated 3 to 5 times. This tag peptide is one which the present inventor previously developed. The tag peptide comprising the tag peptide having a protease recognition sequence in combination with a second tag peptide is characterized in that epitopes of two different antibodies are contained therein, that the two different antibodies can simultaneously bind thereto, and that one of the antibody epitopes overlaps with the protease recognition sequence. The tag peptide having a protease recognition sequence and the second tag peptide may be directly linked to each other. Alternatively, both tag peptides may be linked via any intervening spacer sequence. Hereinafter, the tag peptide according to this embodiment is called "double tag."

Figure 2A:
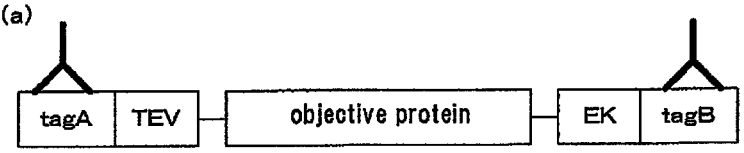
FIG. 2(a) is a schematic view showing sandwich ELISA using two different tag peptides.
Figure 2B:
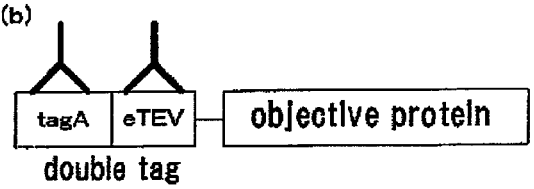
FIG. 2(b) is a schematic view showing sandwich ELISA using a tag peptide comprising the tag peptide having a protease recognition sequence of the present invention in combination with a second tag peptide.

As shown in FIG. 2(a), when sandwich ELISA is usually performed using two different antibodies for detection or quantification of an objective protein, for example, two different tag peptides ("tagA" and "tagB" in FIG. 2(a)) should be linked to the N- and C-termini of the objective protein, and protease recognition sequences ("TEV" and "EK" in FIG. 2(a)) should be separately inserted between the tag peptides and the objective protein, to give a construct of a tag peptide fusion protein. In contrast, in the case of the double tag, sandwich ELISA and removal of the tag peptide by cleavage can be achieved using only one tag peptide. Therefore, the design of a construct can be greatly simplified, and accordingly, the production time and cost of the construct can be significantly decreased. Further, even in the case where an objective protein has a functionally vital structure in the N- or C-terminus and tags cannot be added thereto, the purpose can be attained by addition of the double tag to only one of the termini.

The tag peptide of the present invention can be linked to any protein by a genetic engineering method, and thereby can be formed into a fusion protein of the tag peptide and any protein. In this case, the tag peptide may be linked to the N- or C-terminus of the protein. Such a tag peptide fusion protein in which the tag peptide is linked to the N- or C-terminus of any protein can be highly purified in a single step by use of an antibody that specifically binds to the tag peptide. Further, the tag peptide can be easily removed by cleavage of the purified tag peptide fusion protein. Using the antibody, detection of the tag peptide fusion protein, quantification thereof, etc. can also be performed.

The tag peptide of the present invention can be chemically linked to any substance. Using an antibody that specifically binds to the tag peptide of the present invention, a substance chemically linked to the tag peptide can be highly purified in a simple manner, and its detection, quantification, etc. can also be performed. The substance to be chemically linked to the tag peptide is not limited, and examples thereof include proteins, nucleic acids, saccharides, organic polymers and metals.

The outline of the method for preparing a fusion protein of any protein and the tag peptide of the present invention is as follows.

First, a polynucleotide encoding the tag peptide of the present invention is synthesized according to a known method. The polynucleotide may be DNA or RNA, and is preferably DNA. When the polynucleotide is DNA, it can be synthesized with a DNA synthesizer. Also, DNA fragments separately synthesized may be ligated. The DNA sequence for the tag peptide may be diverse due to degeneracy of the genetic code, and is not particularly limited as long as a peptide expressed from the DNA sequence has the amino acid sequence of the tag peptide of the present invention. Examples of a polynucleotide encoding the eTEV tag include a DNA comprising the base sequence represented by SEQ ID NO: 6. Examples of a polynucleotide encoding the double tag include a DNA comprising the base sequence represented by SEQ ID NO: 7.

Next, a DNA encoding an objective protein is ligated to the 3'- or 5'-terminus of the synthesized DNA encoding the tag peptide. Alternatively, when a DNA encoding an objective protein is prepared by PCR or other methods, the DNA encoding the tag peptide is used as a 3'- or 5'-end primer, to give an objective protein-encoding gene ligated with the DNA encoding the tag peptide as a PCR product.

The obtained DNA, which comprises a DNA encoding the tag peptide and a DNA encoding the objective protein, is appropriately inserted into an expression vector. The vector is not particularly limited, and known expression vectors derived from bacteria, yeasts, viruses or the like can be preferably used. The promoter in the expression vector may be any promoter compatible with hosts used for expression. The expression vector may further comprise an enhancer, a splicing signal, a poly A addition signal, a selection marker and a replication origin. The thus-obtained expression vector is introduced into host cells. The host cell is not particularly limited, and examples thereof include microorganisms such as *Escherichia coli* and yeasts; and animal cells. Preferred are animal cells. The method of introducing the expression vector into host cells can be appropriately selected from known transformation methods depending on the kind of host cells. The obtained recombinant microorganisms or cells are cultured in an appropriate medium for expression of the tag peptide fusion protein. The tag peptide fusion protein can be purified from the recombinant microorganisms or cells, or culture media therefor in a single step by use of an antibody described below.

The present invention also includes a polynucleotide encoding the tag peptide, and a recombinant vector containing the polynucleotide, both of which are illustrated in the above preparation method of the tag peptide fusion protein. The recombinant vector of the present invention is not limited to recombinant vectors that enable expression of a fusion protein of the tag peptide and an objective protein (tag peptide fusion protein), and includes vectors just containing a polynucleotide encoding the tag peptide.

[Antibody]

The present invention provides an antibody against the tag peptide of the present invention. The antibody of the present invention is not particularly limited as long as it recognizes the tag peptide having a protease recognition sequence of the present invention and specifically interacts therewith. The antibody of the present invention can be obtained according to a known method by immunization of mammals such as mice and rabbits using, as an antigen, the tag peptide of the present invention (peptide fragment having a protease recognition sequence). Specific examples of the antibody include antibodies obtainable by immunization of mammals such as mice and rabbits using, as an antigen, an 11-amino-acid-peptide having a TEV protease recognition sequence (RENLYFQGKDC (SEQ ID NO: 8)). Also included is a monoclonal antibody produced by rat-mouse hybridoma 2H5 (internationally deposited at International Patent Organism Depositary, National Institute of Advanced Industrial Science and Technology (central 6, 1-1-1, Higashi, Tsukuba-shi, Ibaraki-ken, 305-8566, Japan) under the accession number FERM BP-11245 on Oct. 31, 2008). Further, a region for antigen recognition excised from such a monoclonal antibody with protease etc. can be used as Fv, Fab or F(ab')$_2$. A recombinant monoclonal antibody can be also produced by use of recombinant technique, specifically by cloning an antibody gene from a hybridoma, inserting the gene into a suitable vector and introducing the vector into a host. The rat-mouse hybridoma 2H5 (FERM BP-11245), which produces the antibody of the present invention, is also included in the present invention.

[Purification Method for Proteins]

The present invention provides a purification method for proteins using the antibody of the present invention. Since the antibody of the present invention specifically interacts with the tag peptide having a protease recognition sequence of the present invention, use of the antibody enables a fusion protein of any protein and the tag peptide of the present invention to be highly purified in a single step. Further, the tag can be easily separated off. The purification method for proteins comprises the following steps (i) to (iii):

(i) making the antibody of the present invention act on a sample containing a fusion protein of an objective protein and the tag peptide of the present invention for formation of a complex of the antibody with the fusion protein;

(ii) making an eluent act on the complex obtained in the step (i) for release of the fusion protein from the antibody; and (iii) separating off the tag peptide by cleavage of the fusion protein obtained in the step (ii).

In the step (i), the sample is not particularly limited as long as it contains a fusion protein of an objective protein and the tag peptide of the present invention. Examples of the sample include a culture supernatant or a cell lysate of transformed cells expressing the fusion protein. When the fusion protein is present in an insoluble fraction such as an inclusion body, solubilization and subsequent refolding of the fusion protein may be appropriately performed. The sample is preferably a sample from which solids have already been removed by centrifugation or the like, and is preferably adjusted to a neutral pH (7 to 8) as needed. The concentration of the objective protein in the sample is preferably 0.2 µg/mL or higher.

In the step (i), use of an immobilized antibody, i.e., the antibody of the present invention immobilized onto a support, is preferable. The support to be used for immobilization of the antibody is not particularly limited as long as the effect of the present invention can be achieved, and known supports can be used. For example, Sepharose (GE Healthcare), Affi-Gel (BIO-RAD), etc. are preferable. The method of immobilizing the antibody onto a support is not particularly limited and can be appropriately selected depending on the kind of the support, etc. For example, for immobilization of the antibody onto Sepharose, the antibody is dialyzed against a coupling buffer and then mixed with CNBr-activated Sepharose (GE Healthcare) at room temperature for about 1 to 2 hours.

Examples of the purification method for proteins in the present invention include both of a column method using the above-mentioned immobilized antibody packed into a column, and a batch method involving mixing the immobilized antibody with a sample for complex formation in a suspension. In the former method, the immobilized antibody is packed into a column, a sample is loaded onto the column, and thereby the antibody of the present invention acts on the tag peptide. In this way, the tag peptide and the antibody bind to each other and thereby a complex of the tag peptide fusion protein and the antibody is formed. In the latter method, about 100 µL of the immobilized antibody is gently mixed with 10 mL of a sample solution. After a complex of the fusion protein and the antibody is formed in the mixture, the mixture is packed into a column.

Then, in the step (ii), an eluent is made to act on the complex obtained in the step (i) for release of the tag peptide fusion protein from the antibody. That is, by an action of the eluent on the complex, the antibody and the tag peptide dissociate, and the tag peptide fusion protein bound to the immobilized antibody via the tag peptide is released from the antibody. As the eluent, any substance that has an action to disrupt the bond between the tag peptide and the antibody of the present invention can be used. Examples of such a substance include water-miscible organic solvents such as polyols, and the tag peptide of the present invention.

For making an eluent act on the complex of the tag peptide fusion protein and the antibody, it is preferable that an elution solution is prepared by mixing the eluent with water or an appropriate buffer solution and then loaded onto the column. In this case, the tag peptide fusion protein released from the antibody by an action of the eluent is eluted together with the elution solution from the column. Water or a buffer solution may be selected depending on the kind of the protein.

Preferably, the eluent content of the elution solution is appropriately varied with the kind of the eluent or the target protein, i.e., the tag peptide fusion protein, or the like. For example, when a water-miscible organic solvent is used as the eluent, the blending ratio of the water-miscible organic solvent is preferably about 30% (v/v) or higher, more preferably about 40% (v/v) or higher relative to the total volume of water or a buffer solution and the water-miscible organic solvent, the total volume being regarded as 100%. The volume ratio of water or a buffer solution to the water-miscible organic solvent (water or buffer solution:water-miscible organic solvent) is preferably about 70:30 to 30:70. In this case, it is desirable that the buffer solution contains a high concentration of a salt, for example, 2 M of NaCl.

When the tag peptide is used as the eluent, the elution solution is preferably prepared so that the concentration of the tag peptide in water or a buffer solution is about 0.01 to 2 mg/mL. More preferred is about 0.03 to 1 mg/mL. As the tag peptide used as the eluent, the tag peptides of the present invention can be used without limitation. The tag peptides of the present invention can be prepared according to a known peptide synthesis method.

After purification of the tag peptide fusion protein, the immobilized antibody is thoroughly washed with the elution solution containing an eluent and thereby can be used repeatedly.

Then, in the step (iii), the tag peptide is separated off by cleavage of the tag peptide fusion protein obtained in the step (ii). That is, a protease that recognizes the protease recognition sequence contained in the tag peptide of the present invention is made to act on the tag peptide fusion protein under suitable conditions, thereby giving an untagged objective protein.

In the purification method for proteins of the present invention, the tag peptide and the antibody specifically interact with each other and the interaction is easily disrupted by an action of an eluent such as the tag peptide and water-miscible organic solvents. Thus, the tag peptide fusion protein can be highly purified in a single step. Further, since a water-miscible organic solvent etc. is used as the eluent, the purification can be performed without any denaturation of the tag peptide fusion protein or the antibody. Furthermore, the tag peptide can be removed by cleavage of the tag peptide fusion protein. Therefore, according to the present invention, high-quality and untagged recombinant proteins suitable for X-ray crystallography are expected to be easily obtainable in sufficient amounts.

[Detection or Quantification Method for Proteins]

By use of the tag peptide and the antibody of the present invention, detection or quantification of an objective protein can be performed. Particularly even in the case where the antibody against an objective protein is not easily available, sandwich ELISA can be performed by use of the double tag and thus a minute amount of the objective protein is detectable. Furthermore, the amounts of an objective protein in plural samples can be compared with one another in a high accuracy. When sandwich ELISA is employed for detection or quantification of a fusion protein of the double tag and an objective protein (hereinafter referred to as "double tag fusion protein"), two different antibodies, i.e., an antibody against the tag peptide having a protease recognition sequence of the present invention (the antibody of the present invention) and an antibody against a second tag peptide are used. In this case, either of the antibodies may be used as a capture antibody and the other one will be a detection antibody. The sample is not particularly limited as long as it contains a double tag fusion protein. Examples of the sample include a culture supernatant or a cell lysate of transformed cells expressing the double tag fusion protein.

The outline of the sandwich ELISA procedure for detection or quantification of a double tag fusion protein is shown in the following.

(1) The detection antibody is modified or labeled by some method in advance. The modifying or labeling method is not particularly limited, and examples thereof include biotinylation, enzyme labeling (such as peroxidase labeling), fluorochrome labeling (such as fluorescein labeling) and radioisotope labeling (such as $^{125}$I labeling).

(2) The capture antibody is immobilized onto microplates.

(3) A sample containing a double tag fusion protein is added over the immobilized capture antibody and the capture antibody is allowed to capture the double tag fusion protein.

(4) Then, the detection antibody is made to act on the double tag fusion protein captured as above and to form a complex therewith. In the case where the detection antibody is enzyme-labeled, the step (6) is performed next.

(5) In the case where the detection antibody is biotinylated, enzyme-labeled streptavidin is made to act on the complex and to bind to biotin of the antibody.

(6) The corresponding chromogenic or luminescent substrate for the enzyme (for example, when the enzyme is peroxidase, the substrate is ABTS) is added. The enzyme catalyzes the cleavage of the substrate to yield a colored reaction product. By measuring the absorbance for each sample, the complex of the double tag peptide fusion protein and the detection antibody can be detected. Since the absorbance is quantitatively correlated with the amount of the double tag peptide fusion protein in the sample, the complex of the double tag fusion protein and the antibody can be quantified. In this case, combined use of a substrate sensitizer with the chromogenic substrate can raise detection sensitivity.

Western blotting can be utilized for detection of an objective protein. In this case, the tag peptide may be a double tag or a tag peptide without a second tag peptide. The outline of the western blotting procedure is shown in the following.

(1) A sample containing a fusion protein of an objective protein and the tag peptide of the present invention is subjected to SDS electrophoresis for separation of the tag peptide fusion protein, and separated proteins are transferred onto a nitrocellulose membrane or a PDVF membrane.

(2) The antibody of the present invention is made to act on the fusion protein on the membrane and to form a complex therewith. In the case where the antibody is enzyme-labeled, the step (4) is performed next.

(3) In the case where the antibody is not labeled with any enzyme, an antibody (enzyme-labeled antibody: secondary antibody) that specifically reacts with the antibody added in the above (2) is made to further act on the complex.

(4) After addition of the corresponding substrate for the enzyme (usually a chromogenic or luminescent substrate), an enzyme reaction product is detected.

The tag peptide and the antibody of the present invention are applicable to the fluorescent antibody method, the immunoprecipitation method, etc. as well as development of detection reagents, cellular imaging, sensor development, etc.

[Kit]

The present invention provides a kit for protein expression, purification, detection or quantification. The kit comprises the recombinant vector or the antibody of the present invention. By use of the kit of the present invention, protein expression, purification, detection or quantification can be simply performed. The kit for protein expression essentially comprises the recombinant vector of the present invention, and the kit for protein purification, detection or quantification essentially comprises the antibody of the present invention. Preferably, the kit of the present invention comprises both the recombinant vector and the antibody of the present invention.

The recombinant vector in the kit for protein expression is preferably provided in such a form that users of the kit can achieve preparation of an expression vector for a tag peptide fusion protein (in which an objective protein and the tag peptide of the present invention are linked to each other) by inserting a DNA encoding the objective protein into a vector. Then, the users can simply achieve expression of the desired protein, i.e., the tag peptide fusion protein by introducing the prepared expression vector into appropriate host cells and culturing the host cells. The antibody of the present invention in the kit for protein purification is preferably immobilized on a suitable support. The kit for protein purification preferably comprises a protease for separation of the tag peptide. More preferred is combining the kit for protein expression and the kit for protein purification into a kit for protein expression and purification.

The kit for protein detection or quantification preferably comprises the antibody of the present invention and an antibody against a second tag peptide which constitutes the double tag. It is also preferable that the antibody of the present invention or the antibody against a second tag peptide in this kit is appropriately labeled (enzyme labeling, radioactive labeling, fluorescent labeling, etc.) or modified (biotinylation etc.). The kit may further comprise a secondary antibody, a reaction buffer solution, a substrate, an instruction manual, etc.

EXAMPLES

Hereinafter, the present invention will be illustrated in detail by examples, but is not limited thereto.

Example 1

Monoclonal Antibody Preparation

An anti-eTEV peptide antibody was prepared by a usual method as follows.

(1-1) Peptide Synthesis and Immunization

An 11-amino-acid peptide (RENLYFQGKDC (SEQ ID NO: 8)) having the TEV protease recognition sequence (ENLYFQG (SEQ ID NO: 3)) and charged amino acids at both ends was synthesized by the Fmoc solid phase method. This eTEV peptide was purified by reversed phase HPLC and then coupled to keyhole limpet hemocyanin (KLH), which is a carrier protein, via the C-terminal cysteine (Cys) residue and the resulting complex was used as an immunogen. Immunization was performed by intracutaneous administration of the eTEV peptide-KLH complex together with an adjuvant (100 µL per foot, 200 µL/animal in total) into the soles of rear feet of a rat (SD, female, 8 weeks old). Two weeks after the immunization, the antibody titer was measured by ELISA. The results showed that the immunization gave a high-titer antibody. From this rat, iliac lymphocytes were isolated and used for cell fusion.

(1-2) Cell Fusion and Hybridoma Establishment

The rat iliac lymphocytes were fused with mouse myeloma cells (SP2/0 cell line) by the polyethylene glycol method, and then cell culture was performed in an HAT selection medium. Using the culture supernatants in wells where a colony was found, ELISA-based screening was performed and strongly positive samples were selected as a candidate for secondary screening. In the secondary screening, a fusion protein (TEV-Fn) described later was used as an antigen. As a result, one highly responsive clone was obtained. The clone was subjected to cloning by limiting dilution, and finally, anti-eTEV antibody producing hybridoma 2H5 was established (internationally deposited at International Patent Organism Depositary, National Institute of Advanced Industrial Science and Technology (central 6, 1-1-1, Higashi, Tsukuba-shi, Ibaraki-ken, 305-8566, Japan) under the accession number FERM BP-11245 on Oct. 31, 2008).

(1-3) Antibody Purification and Preparation of Antibody Immobilized onto Sepharose (1) Antibody Purification The hybridoma 2H5 established in the above (1-2) was cultured in an RPMI1640 medium supplemented with 10% fetal bovine serum. From the culture supernatant, a 2H5 antibody was purified by use of protein G sepharose. The purified antibody was an IgG2a isotype with kappa light chains.

(2) Preparation of Antibody Immobilized onto Sepharose

The purified IgG (about 20 mg) was dialyzed against a coupling buffer (0.1 M $NaHCO_3$, 0.3 M NaCl, pH 8.3) and then mixed with CNBr-activated Sepharose 4B (GE Healthcare), which was washed with 1 mM hydrochloric acid in advance, at room temperature for 1 hour, to give an antibody immobilized onto Sepharose. Unreacted active groups were blocked with 0.1 M Tris, and nonspecifically bound antibodies were removed with 0.1 M Gly-HCl, pH 2.2. The results of quantitative analysis of the unbound antibody showed that about 2 mg of the 2H5 antibody per milliliter of Sepharose resin was able to be immobilized.

Example 2

Preparation of Tag Sequence Fusion Proteins (2-1) Preparation of Tag Sequence Fusion Proteins Using *Escherichia coli* Expression Constructs Using a construct which expresses the 9th to 10th region of the Fn3 domain of human fibronectin (185 residues), constructs for various tag sequence fusion proteins as shown in FIG. 3 were prepared. Each fusion protein has a different TEV-derived sequence (including the eTEV sequence) linked to the N-terminus of the above-mentioned domain. The insert was prepared by extension PCR and then was inserted into the NdeI-BamHI site of the expression vector pET11c (Novagen). Constructs for Ala mutants were prepared by use of Quick Change Mutagenesis kit (Stratagen). *E. coli* BL21 (DE3) cells were transformed with the constructs described above, and expression of the tag sequence fusion proteins was induced by a usual method. The produced fusion proteins were purified from *E. coli* lysates by anion exchange chromatography (for TEV-Fn) or Ni-NTA agarose chromatography (for His-eTEV-Fn etc.).

(2-2) Preparation of Tag Sequence Fusion Proteins Using Animal Cell Expression Constructs pCDNA3.1 (Invitrogen) or an expression vector for human growth hormone (hGH)-fused proteins (pSGHV0, provided by Professor D. Leahy) was used as a vector for expression in mammalian cells. A DNA fragment encoding each target protein and the base sequence encoding the eTEV sequence were ligated by extension PCR, and the obtained fragment was then inserted into the cloning site of the above-mentioned vector. The prepared plasmids were separately transfected into a human cell line HEK293T, and the culture supernatants were subjected to pull-down experiments etc.

Example 3

Characterization of Monoclonal 2H5 Antibody (3-1) Epitope Analysis

The minimum peptide sequence required for recognition by the monoclonal 2H5 antibody (hereinafter referred to as "2H5 antibody") was identified by ELISA using various eTEV-Fn fusion proteins prepared in the above (2-1). The protocol is as follows.
(1) Each His-eTEV-Fn fusion protein (wild type or Ala mutant) solution diluted to 10 μg/mL was added at 50 μL/well to 96-well plates, which were then allowed to stand (4° C., 16 hours).
(2) The supernatant in each well was removed with an aspirator, a 5% skim milk (non-fat milk) solution in Tris-buffered saline (TBS; 20 mM Tris-HCl, 150 mM NaCl, pH 7.5) was added at 200 μL/well, and the plates were allowed to stand at room temperature for 1 hour.
(3) The 2H5 antibody (0.01 to 30 μg/mL) was added at 50 μL/well and the plates were allowed to stand at room temperature for 1 hour.
(4) Each well was washed with 200 μL of TBS 3 times.
(5) A peroxidase-labeled anti-rat IgG (1/1000 dilution) was added at 50 μL/well, and the plates were allowed to stand at room temperature for 30 minutes.
(6) Each well was washed with 200 μL of TBS 4 times.
(7) A peroxidase chromogenic substrate (ABTS) was added at 100 μL/well, the plates were allowed to stand at room temperature for 5 to 10 minute, and then the absorbance of the solution in each well was measured at 405 nm.

The 2H5 antibody was prepared against the synthetic 11-residue peptide (RENLYFQGKDC (SEQ ID NO: 8)) (see Example 1), in which the C-terminal Cys residue was used for coupling with KLH. In this view, the residue(s) essential for antigen recognition is/are theoretically supposed to be within the other 10 residues, except for the C-terminal Cys residue. However, on the ground that the fusion protein TEV-Fn (in which Met and Gly are present at both ends of the 10 residues, see FIG. 3), which was prepared for screening at the very beginning, showed strong binding to the antibody, Ala mutants of this fusion protein were also prepared by substitution of Ala for the terminal amino acids (Met0 and Gly11) and used for analysis. The results are shown in FIG. 4. As shown in FIG. 4, the Ala mutants were divided into three groups in terms of reactivity to the 2H5 antibody. The first group (M0, E2, N3, F6 and Q7) shows exactly the same reactivity as that of the wild-type eTEV peptide. The second group (R1 and G11) shows some reactivity, but 100-or-more times lower reactivity compared with the wild-type eTEV peptide. The third group (L4, Y5, G8, K9 and D10) almost completely lack reactivity. These results showed that the 2H5 antibody recognizes an extremely wide region, that is, the entire 11 residues (RENLYFQGKDG (SEQ ID NO: 2)) of the antigen peptides, and thereby binds thereto. Since the recognition site for anti-peptide antibodies usually consists of several residues, the 2H5 antibody is suggested to have an extremely unique antigen-binding site as an anti-peptide antibody.

(3-2) Relation Between Antigen Recognition Site for the 2H5 Antibody and Recognition Specificity of TEV Protease The eTEV peptide is recognized and cleaved by TEV protease. The amino acid residue(s) essential for recognition by TEV protease was/were identified by use of the above-mentioned series of Ala mutants, which were prepared for determination of the 2H5 antibody epitope. Specifically, each of the His-eTEV-Fn fusion proteins (wild type or Ala mutant) was separately dissolved in TBS at a concentration of 400 μg/mL, a 1/10-fold amount of TEV protease was added, and the reaction was allowed to proceed at 20° C. for 16 hours. SDS was added to stop the reaction, the whole reaction mixture was subjected to SDS electrophoresis on a 15% polyacrylamide gel, and then the gel was stained with Coomassie Brilliant Blue. The cleavage of peptides was evaluated based on the theory that the substrate protein with a molecular weight of 24 kDa shifts in mobility to 20 kDa after cleavage by TEV protease.

The results are shown in FIG. 5. As is clear from FIG. 5, the 4th, 5th and 7th amino acids (namely, Leu, Tyr and Gln) are essential for the substrate of TEV protease, but the other residues are substitutable with Ala. Although these results were mostly consistent with the previous report by Dougherty et al. on the recognition specificity (EMBO J., 7, 1281-1287, 1988), the results revealed new findings, which are not in the report by Dougherty et al.: substitution of Ala for Glu at residue 2 gives no significant change in cleavage; and substitution of an amino acid with a small side chain, such as Ala, for Leu at residue 4 is unacceptable. What is important here is that Gln7 is essential for recognition by TEV protease but unnecessary for recognition by the 2H5 antibody. This shows that changing the 7th residue makes it possible for the characteristics of the peptide to change from the dual recognition mode (recognizable by both of protease and antibody) to single recognition mode.

(3-3) Binding Affinity

Figure 6:
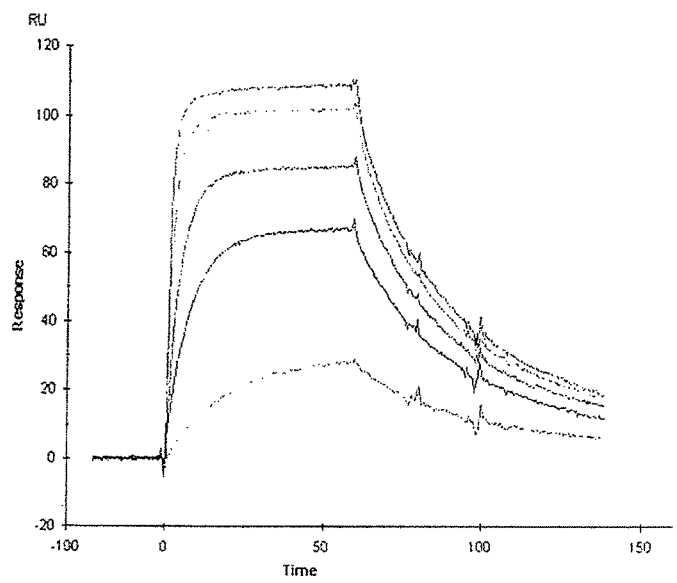
FIG. 6 shows the affinity of the 2H5 antibody for the eTEV peptide based on the results of surface plasmon resonance analysis using Biacore.

For examination on the binding affinity of the 2H5 antibody for the eTEV peptide, surface plasmon resonance analysis using Biacore was performed. After the 2H5 antibody was immobilized on a CM5 sensor chip, the eTEV-Fn fusion protein was made to flow over the prepared sensor chip at various concentrations of 31, 62, 125, 250, 500 and 1000 μM, and the sensorgram was recorded (see FIG. 6). Based on concentration dependency as shown in FIG. 6, the affinity was determined with the BTA evaluation 3.0 program. As a result, the apparent dissociation equilibrium constant was 40 nM, and the affinity of the 2H5 antibody for the eTEV peptide was found to be relatively high.

(3-4) Application to Western Blotting

Figure 7:
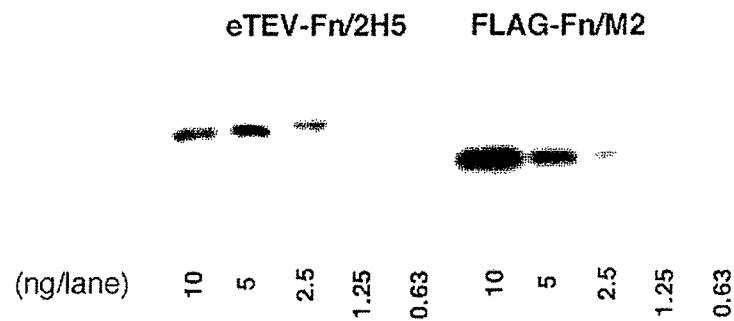
FIG. 7 shows the results of Western blotting using the 2H5 antibody for detection of an eTEV tag fusion protein, and the results of Western blotting using the anti-FLAG antibody. M2 for detection of a FLAG peptide fusion protein.
Figure 10:
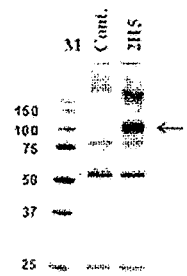
FIG. 10 shows the results of hGH-eTEV-sema6C purification using 2H5 antibody-immobilized sepharose from the culture supernatant of hGH-eTEV-sema6C-expressing HEK293T cells.
Figure 11:
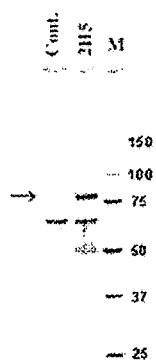
FIG. 11 shows the results of sema3A-eTEV purification using 2H5 antibody-immobilized sepharose from the culture supernatant of sema3A-eTEV-expressing HEK293T cells.

The eTEV-Fn fusion protein (0.63 to 10 ng/lane) was subjected to SDS electrophoresis, transferred on a PDVF membrane, made to react with 1 μg/mL of the 2H5 antibody, and then detected by use of a peroxidase-labeled anti-rat IgG and a chemiluminescence substrate. For comparison, the same amounts of a FLAG peptide fusion protein were subjected to electrophoresis and detected by use of the anti-FLAG antibody M2 (Sigma Aldrich). The results are shown in FIG. 7. As is clear from FIG. 7, the 2H5 antibody can detect the eTEV peptide fusion protein of about 2 ng (0.08 pmol) or more in Western blotting, and its sensitivity is equal to that of the commercial FLAG/M2 system.

Example 4

Pull-Down of Tag Sequence Fusion Proteins Using 2H5 Antibody-Immobilized Sepharose For use in purification of recombinant proteins, the eTEV tag must be able to specifically capture objective proteins in mixtures, such as culture supernatants of expressing cells and E. coli lysates. This ability was examined in pull-down experiments using various constructs.
(Experimental Methods)

Each of various constructs for eTEV-tagged proteins was transiently expressed in HEK293T cells. To 1 mL of the culture supernatant, 20 µL of a 2H5 antibody-immobilized sepharose (hereinafter referred to as "2H5 sepharose") or sepharose alone (control) was added, and then the mixture was allowed to react at 4° C. for 1 hour. After the 2H5 sepharose was precipitated by centrifugation and washed twice with TBS, the objective protein was eluted with an SDS sample buffer and then analyzed as it was by SDS gel electrophoresis. Depending on the molecular weight of the objective protein, the gel of a different acrylamide concentration was used. After electrophoresis, the gel was subjected to Coomassie Brilliant Blue staining or silver staining for protein visualization. The constructs for eTEV-tagged proteins used are as follows.
(1) eTEV-NP1:
the construct for the mouse neuropilin-1 ala2 domain (251 residues) linked to the eTEV tag at the N-terminus
(2) eTEV-EGFP:
the construct for enhanced GFP (241 residues) linked to the eTEV tag at the N-terminus
(3) hGH-eTEV-sema6C:
the construct for a protein having human growth hormone (hGH) at the N-terminus, rat semaphorin 6C (sema6C) at the C-terminus and the eTEV tag in between
(4) sema3A-eTEV:
the construct for mouse semaphorin 3A (sema3A) linked to the eTEV tag at the C-terminus The results of (1) eTEV-NP1, (2) eTEV-EGFP, (3) hGH-eTEV-sema6C and (4) sema3A-eTEV are shown in FIGS. 8, 9, 10 and 11, respectively. In FIGS. 8 to 11, M indicates a molecular weight marker, 2H5 indicates a sample to which the 2H5 sepharose has been added, and Cont. indicates a sample to which the control has been added. The arrow indicates the band of each objective protein. As is clear from FIGS. 8 to 11, tagged proteins expressed from any construct tested were able to specifically bind to the 2H5 sepharose. Strikingly, none of N-terminal (in the case of eTEV-NP1 and eTEV-EGFP), central (in the case of hGH-eTEV-sema6C) and C-terminal (in the case of sema3A-eTEV) addition of the eTEV tag to the objective protein hinders pull-down. This suggests that recognition of the eTEV sequence by the 2H5 antibody is hardly affected by the upstream and downstream structure of the eTEV sequence.

Example 5

Purification of eTEV Tag Fusion Protein Using 2H5 Sepharose (5-1) Examination of Purification Efficiency Single-step purification of an eTEV tag fusion protein of $GFP_{UV}$, i.e., a kind of green fluorescent protein (hereinafter referred to as "eTEV-$GFP_{UV}$") was performed using the 2H5 sepharose. $GFP_{UV}$ is a GFP mutant which has a excitation wavelength shifted towards short wavelengths for easier fluorescent observation with a UV lamp etc. A gene construct encoding a fusion protein having a P4×3 tag, the eTEV sequence, $GFP_{UV}$ of 238 amino acids and a histidine tag in this order from the N-terminus (see FIG. 12, SEQ ID NO: 9) was inserted into the expression vector pET11b for E. coli.

E. coli BL21 (DE3) cells were transformed with the prepared expression vector and expression of the fusion protein was induced by a usual method. Then, 1 mL of the soluble fraction prepared from the transformed cells was loaded onto the 2H5 sepharose (bed volume: 0.5 mL) at 4° C. so that the fusion protein might bind to the 2H5 antibody. After unbound proteins were washed off with TBS, elution was performed with TBS containing 100 µg/mL of the eTEV peptide. Each fraction volume was set to 0.5 mL. As samples, the soluble fraction of E. coli lysates, wash fractions and eluted fractions were subjected to SDS gel electrophoresis.

The results are shown in FIG. 13. In FIG. 13, ori indicates the soluble fraction of E. coli lysates. Samples in lanes 1 to 5 are the wash fractions and samples in lanes 6 to 10 are the eluted fractions. As is shown in FIG. 13, $GFP_{UV}$ is confirmed as a band near 30 kDa in the soluble fraction of E. coli lysates (arrow in FIG. 13). The results showed that the affinity chromatography using the 2H5 sepharose enables $GFP_{UV}$ to be completely purified in a single step. The yield was calculated based on fluorescent measurement (Ex 490 nm/Em 520 nm) of each fraction, and the results showed that about 93% of $GFP_{UV}$ expressed in E. coli was collected in the eluted fractions.

(5-2) Examination of Elution Conditions

The conditions of the buffer solution for elution of eTEV-$GFP_{UV}$ from the 2H5 sepharose were examined. First, the conditions of peptide concentration for competitive elution were examined. The soluble fraction prepared from eTEV-$GFP_{UV}$-expressing E. coil was loaded onto the 2H5 sepharose in the same manner as in the above (5-1). After unbound proteins were washed off with TBS, elution was performed with TBS containing the eTEV peptide at various concentrations of 0 to 1000 µg/mL.

The results are shown in FIG. 14. In FIG. 14, M indicates a molecular weight marker and ori indicates the soluble fraction of E. coli lysates. As is clear from FIG. 14, the eTEV peptide at a concentration as low as 30 µg/ml, enables eTEV-$GFP_{UV}$ to be completely eluted from the 2H5 sepharose. Usually, a 100 to 500 µg/mL peptide solution is used for competitive elution from anti-peptide antibody-immobilized resin. In this view, it is suggested that the purification system for eTEV-tagged proteins using the 2H5 antibody can be established at an extremely low cost.

Next, buffer solutions containing a water-miscible organic solvent and/or a chaotropic ion were examined for the elution ability. The results are shown in FIG. 15. The buffer solutions used are as follows.
Lane 1: TBS containing 0.1 mg/mL eTEV peptide
Lane 2: 40% propylene glycol+2 M NaCl
Lane 3: 40% propylene glycol+2 M NaI
Lane 4: 2 M NaI
Lane 5: 0.1 M Gly-HCl, pH 3.0

As is clear from FIG. 15, elution of eTEV-$GFP_{UV}$ from the 2H5 sepharose was confirmed under the conditions of 40% propylene glycol plus 2 M NaCl (lane 2), and its elution efficiency was about 50% relative to the level under the conditions of TBS containing 0.1 mg/mL of the eTEV peptide (lane 1). Under the conditions of 2 M sodium iodide containing an iodide ion, which is a chaotropic ion, only a slight amount was eluted (lane 4). Under the pH 3.0 acidic conditions, nearly 100% elution was confirmed (lane 5), but dissociation of the antibody from the 2H5 sepharose was also confirmed (band shown by the symbol * in FIG. 15), and thus there is a problem in terms of repeated use of an antibody-immobilized column.

Judging from the above results, in the case of purification, an eTEV peptide solution of 30 µg/mL or higher is suitable for elution of target eTEV tag fusion proteins from the 2H5 sepharose, and a neutral buffer solution containing 40% propylene glycol and 2 M NaCl is suitable for regeneration of resin. It was also confirmed that complete regeneration of resin can be achieved by loading, onto the used column, the above-mentioned neutral buffer solution in a volume 100 times larger than the column volume.

Example 6

Establishment of Double Tag System in Combination with Another Tag

Fusing the eTEV tag and another peptide tag into a continuous tag, namely "double tag" leads to simplification of purification, sandwich ELISA or the like for recombinant proteins. For confirmation of this potential, a 33-amino-acid tag sequence (SEQ ID NO: 10, hereinafter referred to as "W tag") in which a target tag and the eTEV tag are linked to each other as shown in FIG. 16 was designed, and then expression of proteins fused with this tag sequence was induced. Specifically, expression of $GFP_{UV}$ or Fn fused with the W tag at the N-terminus was induced in *E. coli*, the expressed protein was purified, and then sandwich ELISA was performed in the following manner.

10 µg/mL of a P20.1 antibody (mouse IgG), which is an anti-target tag antibody, was immobilized to microtiter plates. After blocking, a solution of the purified W tag fused $GFP_{UV}$ (W-$GFP_{UV}$) or W tag fused Fn (W-Fn) was diluted to concentrations of 0.003 to 3 µg/mL and added to wells of the plates. The plates were then allowed to stand at 4° C. overnight so that the fusion protein might be captured by the antibody. After washing, a biotinylated 2H5 antibody (5 µg/mL) was made to react with the fusion protein at room temperature for 30 minutes. After 3-time washing, peroxidase-labeled streptavidin (Zymed) was added to the plates, which were then allowed to stand at room temperature for additional 15 minutes. After addition of a peroxidase substrate (ABTS), the absorbance at 405 nm was measured.

Figure 17:
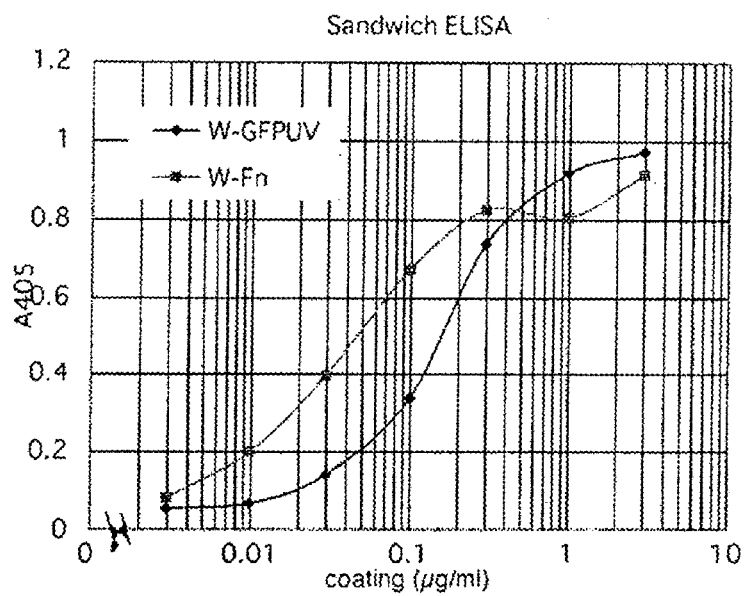
FIG. 17 shows the measurement results of double tag fusion proteins in sandwich ELISA.

The results are shown in FIG. 17. As is clear from FIG. 17, in the sandwich ELISA using two different antibodies, the two kinds of proteins fused with the W tag showed a favorable concentration dependent signal and were quantifiable at concentrations of 1 µg/mL or lower. This shows that, to adjacent tag sequences, two respective antibodies can simultaneously bind. However, since there is an about 3-fold difference between W-$GFP_{UV}$ and W-Fn in the concentration dependency in the sandwich ELISA, it is suggested that the property and structure of a fusion partner protein can affect the binding of the P20.1 antibody or the 2H5 antibody to the tag sequence.

It was also confirmed that the above-mentioned W tag fusion proteins, like single tag fusion proteins, can be used for affinity purification using the P20.1 antibody or the 2H5 antibody and for cleavage by TEV protease. Therefore, it was concluded that the W tag can play a double role as desired.

Example 7

Quick Screening for Stably Expressing Cell Using W Tag

Figure 18:
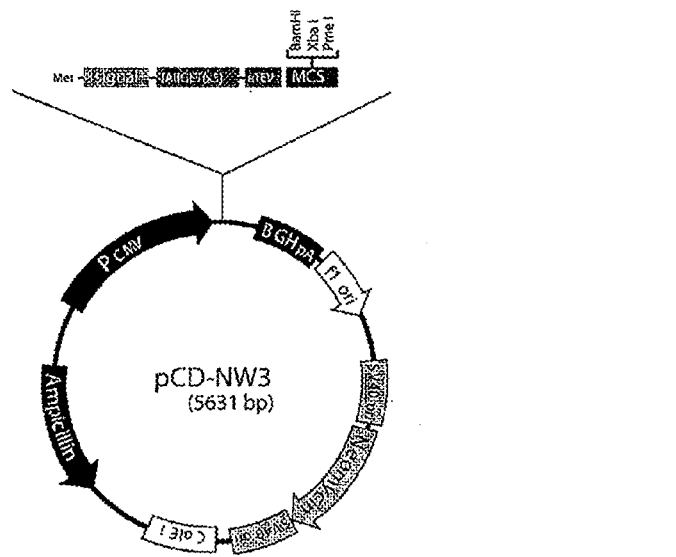
FIG. 18 shows the construct of the expression vector pCD-NW3 for double tag fusion proteins.

Expression vectors for W tag fusion proteins were constructed and transfected into HEK392T cells or HEK293SGnT1-cells, and strains highly expressing the objective protein were screened for. pCD-NW3 was used as an expression vector (see FIG. 18). A Dulbecco MEM medium supplemented with 10% fetal bovine serum and 1 mg/mL G418 was used as the culture medium. Screening was performed using the same sandwich ELISA as described in Example 6. Specifically, 10 µg/mL of the P20.1 antibody was immobilized to microtiter plates, and after blocking, the culture supernatant was added to wells of the plates. The plates were then allowed to stand at 4° C. overnight so that the fusion protein might be captured by the antibody. After washing, the biotinylated 2H5 antibody (5 µg/mL) was made to react with the fusion protein at room temperature for 30 minutes. After 3-time washing, peroxidase-labeled streptavidin (Zymed) was added to the plates, which were then allowed to stand at room temperature for additional 15 minutes. After addition of the peroxidase substrate (ABTS), the absorbance at 405 nm was measured.

(7-1) Autotaxin (Cancer-Cell-Metastasis Promoting Factor) Expressing Cell

Figure 19A:
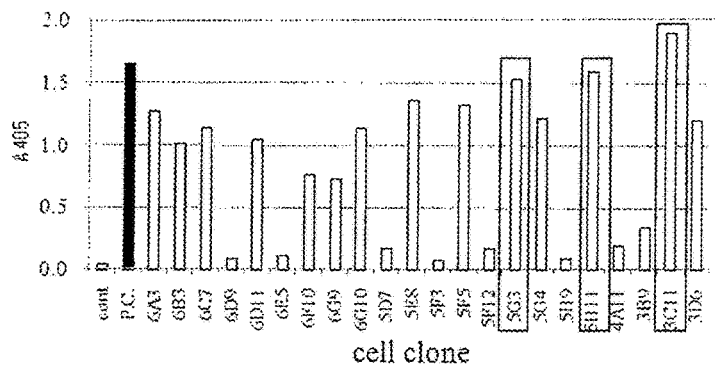
FIG. 19(a) shows the results of primary screening for the autotaxin-high-expressing strain.
Figure 19B:
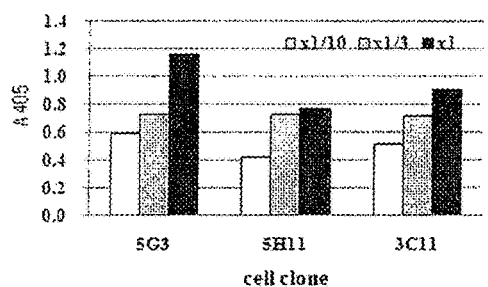
FIG. 19(b) shows the results of secondary screening for the autotaxin-high-expressing strain.

An expression vector for autotaxin fused with the W tag at the N-terminus was constructed and then transfected into HEK293SGnT1-cells. The cells were cultured for 20 days for selection of G418-resistant cells and then the obtained clones were subjected to primary screening. The results of the primary screening are shown in FIG. 19(*a*). Three clones with a high expression level of autotaxin (5G3, 5H11 and 3C11) were selected and then subjected to secondary screening. In the secondary screening, non-diluted, 3-fold diluted and 10-fold diluted culture supernatants of each clone were used as samples. The results of the secondary screening are shown in FIG. 19(*b*). Based on the results of the secondary screening, clone 5G3 was selected as an autotaxin-high-expressing strain.

Figure 20:
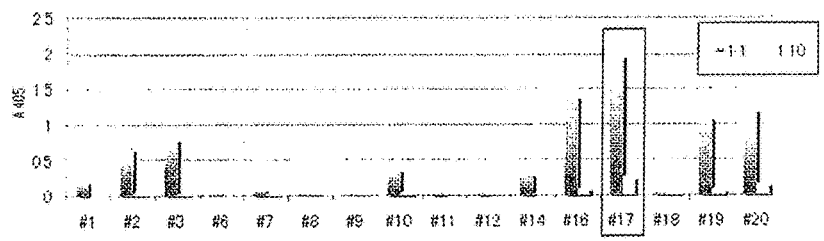
FIG. 20 shows the results of screening for the CRISPa-high-expressing strain.

(7-2) CRISPa (Cysteine-Rich Secretory Protein a, Snake Venom Vascular Permeability Factor) Expressing Cell An expression vector for CRISPa fused with the W tag at the N-terminus was constructed and then transfected into HEK392T cells. The cells were cultured for 12 days for selection of G418-resistant cells and then the obtained clones were subjected to screening. The results of the screening are shown in FIG. 20. Based on the results of the screening, clone #17 was selected as a CRISPa-high-expressing strain.

(7-3) Semaphorin 3A (Neuronal Guidance Factor) Expressing Cell

Figure 21A:
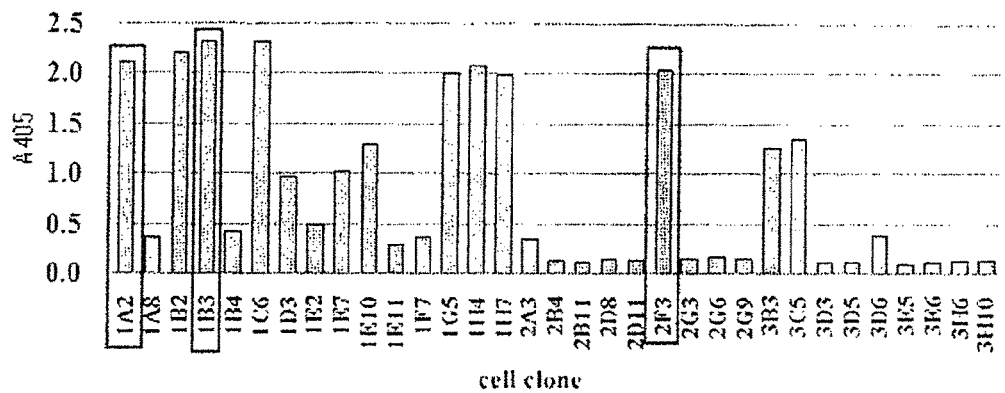
FIG. 21(a) shows the results of primary screening for the semaphorin 3A-high-expressing strain.
Figure 21B:
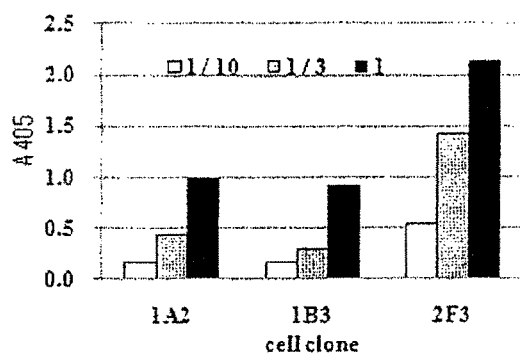
FIG. 21(b) shows the results of secondary screening for the semaphorin 3A-high-expressing strain.

An expression vector for semaphorin 3A fused with the W tag at the N-terminus was constructed and then transfected into HEK392T cells. The cells were cultured for 14 days for selection of G418-resistant cells and then the obtained clones were subjected to primary screening. The results of the primary screening are shown in FIG. 21(*a*). Three clones with a high expression level of semaphorin 3A (1A2, 1B3 and 2F3) were selected and then subjected to secondary screening. In the secondary screening, non-diluted, 3-fold diluted and 10-fold diluted culture supernatants of each clone were used as samples. The results of the secondary screening are shown in FIG. 21(*b*). Based on the results of the secondary screening, clone 2F3 was selected as a semaphorin 3A-high-expressing strain.

As described above, even in the case where the antibody against an objective protein is not easily available, use of the W tag enables accurate detection and comparison of the objective protein expression level, and simple screening for strains highly expressing the objective protein.

The present invention is not limited to the aforementioned embodiments and examples, and various modifications can be made within the scope of the appended claims. Other embodiments obtainable by suitably combining technical means disclosed in different embodiments of the present invention are also included in the technical scope of the present invention. All the academic publications and patent literature cited in the above description are incorporated herein by reference.

INDUSTRIAL APPLICABILITY

The present invention is applicable to a system by which recombinant proteins can be highly purified in an easy manner at low cost, and therefore, is useful in industries utilizing recombinant proteins, such as pharmaceutical industry, research reagent industry and food industry.

[Accession Number]
Hybridoma 2H5 FERM BP-11245

The invention claimed is:

1. An antibody against a tag peptide having a protease recognition sequence overlapping with an epitope of the antibody against the tag peptide, wherein the tag peptide consists of the amino acid sequence of SEQ ID NO: 2.

2. The antibody according to claim 1 which is a monoclonal antibody produced by rat-mouse hybridoma 2H5 (FERM BP-11245).

3. Rat-mouse hybridoma 2H5 (FERM BP-11245).

4. A kit for protein purification, detection or quantification, comprising the antibody according to claim 1.

* * * * *